United States Patent [19]
Potter
[11] Patent Number: 4,781,704
[45] Date of Patent: Nov. 1, 1988

[54] FEEDING TUBE ASSEMBLY WITH COLLAPSIBLE OUTLET CONNECTOR

[75] Inventor: Laurence A. Potter, Whitehouse Station, N.J.
[73] Assignee: Entech, Inc., Lebanon, N.J.

[21] Appl. No.: 18,157
[22] Filed: Feb. 24, 1987
[51] Int. Cl.[4] .......... A61M 31/00
[52] U.S. Cl. .......... 604/270; 604/264; 604/281; 604/105
[58] Field of Search ........ 604/270, 264, 266, 275–276, 604/277, 280–281, 283–284, 105–106

[56] References Cited

U.S. PATENT DOCUMENTS

| | | | |
|---|---|---|---|
| 686,281 | 11/1901 | Gerry | 604/270 |
| 781,763 | 2/1905 | Bowker | 604/105 |
| 806,746 | 12/1905 | Miller | 604/274 |
| 1,899,781 | 2/1933 | Twiss | 604/270 |
| 2,097,039 | 10/1937 | Peterson | 128/347 |
| 4,228,802 | 10/1980 | Trott | 604/105 |
| 4,301,796 | 11/1981 | Child | 604/105 |
| 4,315,513 | 2/1982 | Nawash et al. | 604/283 |
| 4,351,342 | 9/1982 | Wiita et al. | 128/349 B |
| 4,490,138 | 12/1984 | Lipsky et al. | 604/264 |
| 4,490,143 | 12/1984 | Quinn et al. | 604/270 |
| 4,516,970 | 5/1985 | Kaufman et al. | 604/270 |
| 4,559,046 | 12/1985 | Groshong et al. | 604/105 |
| 4,594,074 | 6/1986 | Andersen et al. | 604/270 |
| 4,601,724 | 7/1986 | Hooven et al. | 623/66 |
| 4,610,673 | 9/1986 | Russo | 604/270 |
| 4,668,225 | 5/1987 | Russo et al. | 604/270 |

*Primary Examiner*—C. Fred Rosenbaum
*Assistant Examiner*—Gene B. Kartchner
*Attorney, Agent, or Firm*—Lerner, David, Littenberg, Krumholz & Mentlik

[57] ABSTRACT

An enhanced non-occluding feeding assembly for the administration or aspiration of fluids to a patient comprising a tube having an enlarged, resilient bolus near its distal end to which a weighted tip is connected is provided. The bolus defines an opening for the tube outlet minimizing occlusion or clogging of the opening. The feeding assembly provides advantageous peristaltic or stylet intubation and minimizes possibility of injury to a patient.

15 Claims, 2 Drawing Sheets

FEEDING TUBE ASSEMBLY WITH COLLAPSIBLE OUTLET CONNECTOR

TECHNICAL FIELD

The present invention generally relates to the internal administration, irrigation and aspiration of fluids to and from body cavities of patients and, in particular, to an improved enteral feeding tube assembly therefor.

BACKGROUND OF THE INVENTION

Enteric therapy of patients involves administering fluid nutrients and various medical preparations through a flexible feeding tube into the gastrointestinal tract. Such feeding tubes are inserted either nasally, surgically, percutaneously, or orally, and, therefore, must be of a small cross sectional diameter. Nasogastrointestinal tubes are inserted into a patient's nostril, guided through the nasopharynx and oropharynx into the esophagus. The tube then advances into the patient's stomach or duodenum either by peristaltic movement or by the use of an internal guide or stylet.

Typically, enteral feeding is utilized when patients are unable to swallow or are having difficulty masticating or otherwise are unable to achieve adequate nutritional intake. By using an enteral feeding tube to supply nutrient fluids to patients, the risks of intravenous hyperalimentation, viz., sepsis or metabolic derangement, are avoided.

Various types of feeding tubes have been utilized for the enteric therapy of patients. For example, U.S. Pat. No. 1,899,781 issued Feb. 28, 1933 to J. R. Twiss, describes a stomach tube having a hollow metal bucket forming the tube outlet. The bucket exhibits a concave formation with the intermediate portion of the bucket having a considerably reduced diameter with respect to the end portions or shoulders. A ball weight is attached to the distal end of the bucket and tube, and serves to anchor the tube in the patient's stomach. This feeding tube, however, may cause patient discomfort during intubation. In addition, due to the shape and small openings of the bucket, this tube is more susceptible to clogging by coagulated matter.

Another feeding tube, described in U.S. Pat. No. 4,516,970 issued May 14, 1985 to Kaufman et al., contains staggered apertures in the walls of the distal end of the tube. These apertures permit the flow of fluids from the tube; however, they also serve to weaken the tube wall, resulting in a greater likelihood of the wall collapsing, twisting or bending. Any of these conditions would cause interference with the flow of fluids into and out of the tube and could also cause difficulties with the progression of the tube during intubation.

U.S. Pat. No. 4,351,342 issued Sept. 28, 1982 to Wiita et al., describes a tube having an enlarged tip at its distal end. This enlarged tip may cause pain to a patient during intubation and may permit the accumulation of fluids, resulting in coagulation and clogging of the tube.

To provide for easier intubation, Quinn et al., in U.S. Pat. No. 4,490,143 issued Dec. 25, 1984, describe a flexible feeding tube having an internally weighted guide tip at its distal end. The feeding tube has a bead-like bolus located proximal to the guide tip. The bolus contains lateral apertures which permit the flow of fluids to and from the tube. More specifically, the bolus is partially hollow and contains a cylindrical channel which is perpendicular to the tube lumen. At least two openings are formed at the ends of the cylindrical channel, thereby permitting the passage of fluids. In addition, the bolus provides a rigid housing for the distal end of a stylet during intubation. Although this feeding tube assembly provides for somewhat easier intubation, the relatively small openings in the bolus are very susceptible to fluid flow restriction and clogging.

On attempt to deal with these problems was disclosed in U.S. Pat. No. 4,594,074 issued June 10, 1986 to Andersen et al. Andersen et al. utilize an enteral feeding tube having a tubular shaped, non-collapsible bolus on the distal end of the tube. This bolus has at least one outlet opening for fluid communication through its side wall. The side walls of the bolus are upright and vertical, reducing the likelihood of the tube bolus collapsing. To maximize fluid flow and minimize occlusion, the side walls of the bolus opening are recessed to provide for a larger outlet. The passage of the bolus contains an upwardly inclining floor to regulate the stream of fluids from the tube.

One problem encountered in all the above prior art enteral feeding tubes is the difficulty of intubation when moderate restrictions are encountered. For example, a tube bolus must be forced past a tissue growth or tumor to achieve placement in a patient's stomach. This situation may cause great discomfort and pain to a patient.

Another problem encountered with prior art tubes is the occlusion of the tube outlet with gastrointestinal debris or coagulated matter. The outlets of prior art tubes may also become blocked during aspiration by being drawn up against the mucosal lining of the gastrointestinal tract.

As recognized by those in the industry, the most preferred design of an enteral feeding tube to achieve a maximum rate of fluid flow out of the tube, would be an open-ended tube. Such a tube, however, would be susceptible to occlusion, especially during aspiration, and could easily become caught against the mucosal lining making intubation difficult. Accordingly, an elongated guide tip or distal end weighted tip would be desirable in conjunction with an open-ended tube. These end tips aid intubation and minimize trauma to the mucosal linings of the gastrointestinal tract.

Hence, prior to the development of the present invention, a need existed for an interal feeding tube which could be inserted with minimal discomfort or risk to the patient and would not become occluded with fluid nutrients, medical preparations, or mucous.

SUMMARY OF THE INVENTION

According to the present invention, a feeding tube assembly for the administration of fluids to patients has been developed utilizing a uniquely designed outlet connector or bolus disposed on a distal end of the tube. The bolus defines an opening for the tube outlet and is designed to substantially approximate the fluid flow characteristics of an open-ended tube while providing the advantage of preventing occlusion of the opening with mucous and feeding materials. In addition, the shape and features of the bolus alleviate the difficulties of intubation, in particular, patient discomfort and risks of tissue damage.

In a broad sense, the present invention embodies a feeding assembly comprised of a flexible tube with an internally weighted guide tip located at the distal end. The guide tip has the same or slightly less cross-sectional diameter than the corss-sectional diameter of the tube. This guide tip is designed for easier and less painful intubation of patients. The guide tip encases cylindrical segments of tungsten or similar material, which provide weight and rigidity as well as flexibility for intubation. The tungsten is non-toxic to a patient and resists degradation by gastric acids.

The distal outlet portion of the tube is connected to an enlarged bolus located proximal to the guide tip and made from a biocompatible thermoplastic material. This bolus provides an enlarged opening outlet which permits the release or passage of fluids from the tube, while preventing the occlusion of the tube outlet with coagulated feeding materials. In addition, during intubation the shape of the bolus enhances peristaltic advancement of the tube. The resiliency of the bolus also provides flexibility around tissue barriers thereby preventing soft tissue damage.

The present invention is further described and disclosed with reference to a preferred embodiment presented in the drawings and set forth below in the written description.

DETAILED DESCRIPTION

Figure 1:
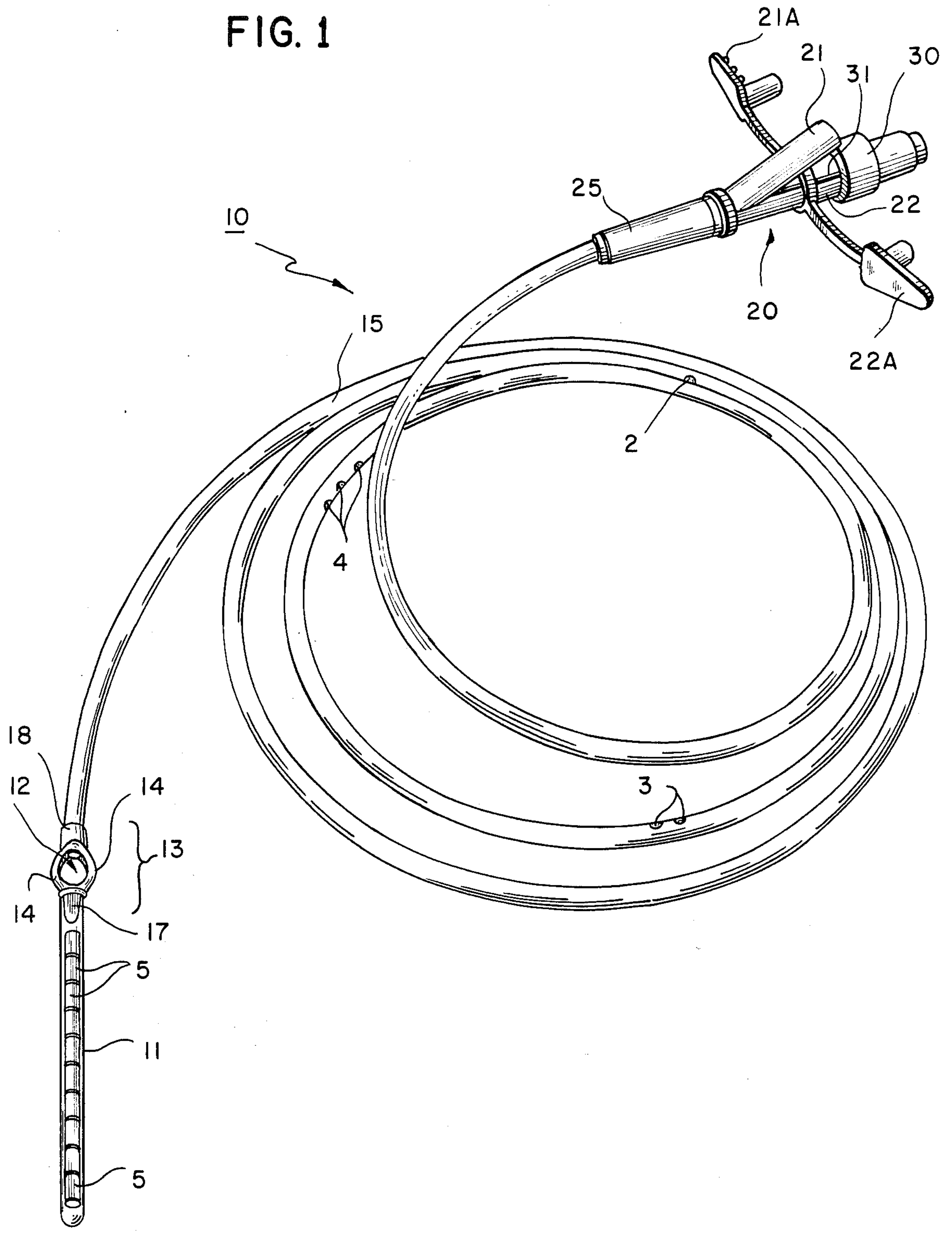
FIG. 1 is a perspective view of an embodiment of the present invention showing application of the collapsible bolus of FIG. 2 in an enteral feeding tube.

Referring now to the drawings, FIG. 1 illustrates the feeding tube assembly of the present invention generally referenced by the numeral 10. Feeding tube assembly 10 is of a linear tubular shape generally used in the art and is inserted into the nasal cavity of a patient. Once the feeding tube assembly 10 has been inserted nasally, the feeding tube assembly 10 passes through the patient's throat or pharynx into the esophagus. Peristaltic action or stylet insertion aid in further progression of the tube assembly 10 into the patient's intestinal tract.

Feeding tube assembly 10 includes a guide tip 11 and flexible, hollow tube 15. Assembly 10 further includes an enlarged, flexible bolus 13 located between guide tip 11 and the distal end of hollow tube 15. Bolus 13 possesses a larger cross-sectional diameter than the cross-sectional diameter of tube 15. This enlarged cross-sectional diameter, defined in one dimension by sides 14 and opening 12, provides an aid to peristaltic intubation; while the flexibility of bolus 13 enhances comfort and safety during insertion. Bolus 13 is smoothly contoured, having enlarged opening 12 to allow for the easy entry or exit of fluids in and out of tube 15.

"Y-shaped" connector 20 is attached to the proximal end of hollow tube 15 by adapter sleeve 25 and provides means for the administration of fluids into tube assembly 10. For this purpose, connector 20 includes twin ports 21 and 22, which aid in making tube assembly 10 anticloging and provide an inlet/outlet function. Ports 21 and 22 are standard female luer tapers. Connector 20 enables a "closed system" technique whereby port 22 remains attached to feeding tube assembly 10 and serves as the administration port, while port 21 can simultaneously be utilized as an irrigation/aspiration port. Once the tube assembly has been properly placed in the patient's intestinal tract, the administration port 22 is attached to an administration set, e.g., a feeding bag and pump setup, such that fluids can be administered to the patient at a desired rate.

More specifically, connector 20 is designed such that medicines or formulas can be administered, or the tube assembly irrigated, through port 21, while never having to disconnect the administration set from port 22. Connector 20 can also be used to confirm tube placement and insure tube patency with luer tip/lock syringes. Accordingly, connector 20 may be made of clear, flexible vinyl for ease in visual verification of gastric residuals and fluid delivery.

When ports 21 and 22 are not in use, they may be closed off with caps 21A and 22A, respectively. To provide stylet insertion of feeding tube assembly 10, braided stylet 31 is pre-lubricated and inserted into the proximal end of tube 15, through port 22. Stylet 31 is used to guide the feeding tube assembly 10 during insertion and aid in proper placement. The stylet 31 is generally of a length less than or equal to the length of tube 15 so that there is no danger of the stylet protruding through bolus opening 12 thereby risking internal injury to the patient. Typically, stylet intubation is utilized when a patient is unable to swallow or otherwise aid in the progression of the tube.

Stylet 31 is connected to cap 30 which extends beyond the end of port 22, thereby providing ease in stylet-aided intubation and withdrawal. The pre-lubrication and pre-insertion of stylet 31 within tube 15 provide an advantage over prior art assemblies in that no additional intubation procedural steps, such as water activation or lubricating the tube lumen, are necessary. Cap 30 may be color-coded for easy discernment of information such as tube and/or stylet size or length. Such visual information can also be indicated on adapter sleeve 25.

Hollow tube 15 is manufactured from any biocompatible thermoplastic material, such as polyurethane, to provide in vivo stability in addition to flexibility. This medical grade polyurethane withstands high PSI to prevent the problems inherent in tube bursting-/aneurysms. Some type of radiopaque marker, such as barium sulfate or bismuth trioxide, is blended in with the tube material so that, if desired, the tube assembly 10 can be clearly detected by x-ray.

The outer surface of tube 15 contains dots 2, 3, and 4 which serve as reference marks to aid in intubation. For example, dots 2, 3, and 4 are located twenty inches, twenty-five inches and thirty inches, respectively, from the distal end of tube 15. These markers then serve as a placement aid for the physician, who can observe the approximate length of tube which has been inserted so far.

Figure 2:
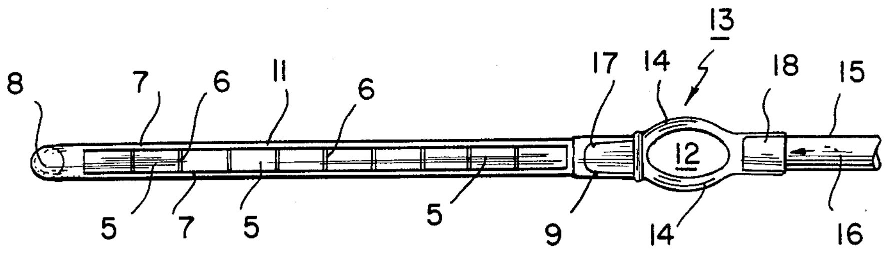
FIG. 2 is plan view of one embodiment of the collapsible bolus and guide tip of the present invention.

FIG. 2 illustrates the novel structure of feeding tube assembly 10 of the present invention. Tube 15 is connected to bolus 13 with the distal end of tube 15 being inserted into open end 18 of bolus 13, and solvent bonded or otherwise appropriately sealed therein. The open distal end of tube 15 is thereby unobstructively aligned with opening 12 of bolus 13, and in fluid communication therewith. More specifically, fluid passing through the tube lumen 16 (i.e., the tubular cavity defined by the walls of tube 15) exits tube 15 and bolus 13 through opening 12 and is dispensed into the gastrointestinal tract.

The cross-sectional diameter of bolus 13 is defined in one dimension by opening 12 and sides 14. In order to provide the highest fluid flow dynamics, the diameter of bolus 13 is designed to be approximately three times the size of the inside diameter of tube 15. The bolus 13 with enlarged opening 12 thereby simulates the flow characteristics of an open-ended tube. In addition, the structure of the present invention lacks physical barriers upon which food or medications can coagulate, thereby further preventing occlusion of tube 15 and feeding assembly 10.

Figure 3:
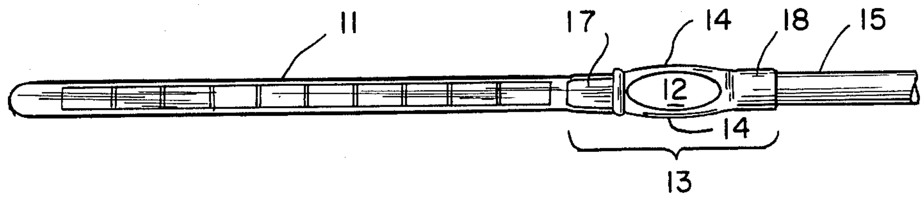
FIG. 3 is a plan view of an embodiment of the present invention showing the bolus in a collapsed position.

To provide resiliency, bolus 13 is made of a biocompatible thermoplastic material which is molded or heat set to a specific configuration. According to the present invention, bolus 13 is enlarged only in one plane (as defined by opening 12 and sides 14) as opposed to being enlarged around the entire circumference as in prior art assemblies. As shown in FIG. 3, this design permits sides 14 of bolus 13 to collapse or deform, providing flexibility when necessary, e.g., when a tumor or other restriction is encountered during intubation. Once bolus 13 is past such an obstruction, bolus 13 will reopen and resume its original shape.

Figure 4:
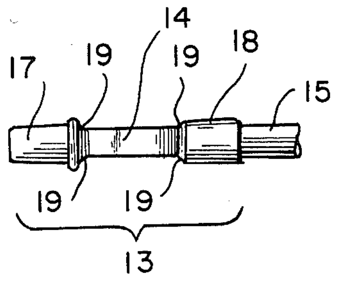
FIG. 4 is a perspective view of the bolus as seen from one side.

The enlarged shape of bolus 13 acts as an aid in the peristaltic progression of feeding tube assembly 10 into the gastrointestinal tract. In addition, as shown in FIG. 4, sides 14 contain bevels 19 along the top and bottom of both the proximal and distal edges of opening 12. Bevels 19 provide a smooth contour for bolus 13 and further prevent the scraping of soft tissue during intubation.

Figure 5:
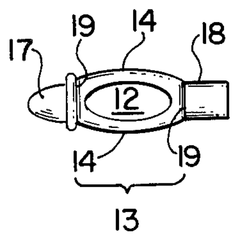
FIG. 5 is a plan view of an embodiment of the present invention showing the bolus having a radius blunt tip end.

The proximal end 17 of bolus 13 is closed off to form a plug. As shown in FIG. 5, for applications where an unweighted end is desired, bolus 13 can be used as a stand-alone, unweighted outlet connector by forming plug end 17 as a smoothly contoured radius blunt tip. For applications where some type of guide tip is desired, however, plug end 17 can easily be connected to such a guide tip. For example, as shown in FIG. 2, open-end 9 of guide tip 11 is inserted over bolus plug end 17 and suitably sealed or solvent bonded thereto, such that no fluids can accumulate at the distal end of bolus 13 but are fully dispersed into the gastrointestinal tract.

Guide tip 11 has an open proximal end 9 which is bonded to bolus plug end 17, and a sealed blunt tip 8 at its distal end. The tubular walls 7 of guide tip 11 encase cylindrical, rod-like segments 5. Cylindrical segments 5 are made of tungsten or other similar non-toxic, high specific gravity, and internally inert material, and aid in the gravity placement of feeding tube assembly 10; aid in the peristaltic progression of tube assembly 10 into the gastrointestinal tract; and prevent involuntary regurgitation of tube assembly 10. Cylindrical segments 5 are positioned laterally within guide tip 11, with spaces 6 formed between the segments. These spaces 6 enable guide tip 11 to be flexible, while simultaneously maintaining some degree of rigidity. If greater flexibility is desired, more cylindrical segments 5 can be included within the guide tip 11. Solder or other maleable types of metal can also be inserted into spaces 6 inbetween segments 5 to provide pliability while retaining some desired shape. Alternatively, guide tip 11 can be formed into a pre-set curved shape such that correct intubation is enhanced. For example, the guide tip could be specifically shaped to facilitate placement of the tube assembly through a patient's esophagus while preventing misplacement of the tube assembly down the patient's trachea.

Guide tip 11 is pre-lubricated or coated with a hydrophilic polymer. Prior to insertion of feeding tube assembly 10 into a patient, guide tip 11 is dipped in water, activating the lubricant, thereby providing for easier intubation.

Although the present invention has been described with reference to a preferred embodiment, it should be understood by those in the art that various changes or substituted equivalents are within the scope of the invention. It is therefore intended that the invention not be limited to the particular embodiment or application disclosed herein as the best mode for practicing the invention, but will include all embodiments covered within the scope of the claims.

What is claimed is:

1. An enteral feeding tube of predetermined diameter for administration and aspiration of fluids within a gastrointestinal tract, said tube having a proximal end for fluid communication with a fluid nutrient source and a distal end comprising a bolus positioned at the distal end of said tube, said bolus being enlarged in a first dimension and having resilient sides defining an opening, said bolus being intersected by a first longitudinally extending plane and a second plane substantially transverse to said first plane, said first dimension being defined by said first plane, whereby said bolus is normally enlarged in said first plane and not in said second plane, said bolus having a first end in fluid communication with said tube and a terminal end, said bolus having a diameter greater than the diameter of said tube thereby increasing the flow of fluid from said fluid nutrient source during administration, said sides being collapsible upon contact with a restriction and being capable of resuming their original shape upon passing said restriction, thereby temporarily reducing the diameter of said bolus.

2. A feeding tube as in claim 1, wherein said terminal end of said bolus is sealed, thereby minimizing the accumulation of fluids at said terminal end.

3. A feeding tube as in claim 1 wherein said opening has beveled edges.

4. A feeding tube as in claim 1, further comprising a guide tip connected to said terminal end of said bolus.

5. A feeding tube as in claim 4, wherein said guide tip is weighted.

6. A feeding tube as in claim 4, wherein said guide tip has a diameter less than the diameter of said bolus and less than or equal to the predetermined diameter of said tube.

7. A feeding tube as in claim 4, wherein said guide tip encases cylindrical rod-like segments of a non-toxic, relatively dense and internally inert material.

8. A feeding tube as in claim 7, wherein said rod-like segments are comprised of tungsten.

9. A feeding tube as in claim 7, wherein said guide tip also encases a malleable metal material inbetween said cylindrical rod-like segments.

10. A feeding tube as in claim 4, wherein said guide tip is formed into a preset curved shape.

11. A feeding tube as in claim 1, further comprising a stylet inserted into the proximal end of said tube.

12. A feeding tube as in claim 1, further comprising an adapter at the proximal end of said tube, said adapter having at least two ports.

13. A feeding tube as in claim 12, wherein a first port is connected to the fluid nutrient source and a second port allows the instillation or irrigation of fluids.

14. A catheter of predetermined diameter for irrigation and aspiration of fluids within body cavities, said catheter having a proximal end for fluid communication with a fluid or suction source and a distal end having an outlet, said distal end comprising a bolus in fluid communication with said outlet, said bolus having resilient sides defining an opening which permits fluid flow through said outlet and said bolus from or into said body cavities, said bolus being intersected by a first longitudinally extending plane and a second plane substantially transverse to said first plane, said bolus being enlarged in a first dimension defined by said first plane and not being enlarged in a second dimension defined by said second plane, said bolus having a diameter greater than the diameter of said outlet thereby increasing the flow of fluid from said fluid nutrient source said sides being are collapsible from an original shape and reconformable back into said original shape.

15. A catheter as in claim 14, further comprising a weighted guide tip connected to said bolus.

* * * * *